United States Patent [19]

Siegel et al.

[11] Patent Number: 5,662,866
[45] Date of Patent: Sep. 2, 1997

[54] TWO COMPARTMENT CUP FOR POWDERED STERILANT REAGENT COMPONENTS

[75] Inventors: Norman L. Siegel, Mentor; Lewis I. Schwartz, Bratenahl; Raymond C. Kralovic, Willoughby; Joseph J. Switka, Garfield Heights; Craig M. Saunders, Rocky River; Nick E. Stanca, Westlake; Gregory A. Dale, Grafton; Jeffrey S. Plantz, Seven Hills, all of Ohio

[73] Assignee: Steris Corporation, Mentor, Ohio

[21] Appl. No.: 533,245

[22] Filed: Sep. 25, 1995

[51] Int. Cl.⁶ ............................................ A61L 9/00
[52] U.S. Cl. ......................... 422/29; 206/538; 422/292; 422/294
[58] Field of Search .................................. 422/292, 294, 422/29, 102; 206/221, 568, 531, 538, 467, 506

[56] References Cited

U.S. PATENT DOCUMENTS

| | | |
|---|---|---|
| 1,072,351 | 9/1913 | Munson ........................... 422/294 X |
| 2,494,456 | 1/1950 | Still ................................. 128/272 |
| 4,171,340 | 10/1979 | Nishimura et al. ............... 422/36 |
| 4,482,047 | 11/1984 | Ackermann et al. ............. 206/219 |
| 4,483,439 | 11/1984 | Steigerwald et al. ............ 206/219 |
| 4,869,387 | 9/1989 | Persson .......................... 220/20.5 |
| 5,037,623 | 8/1991 | Schneider et al. ............... 422/292 |
| 5,209,909 | 5/1993 | Siegel et al. .................... 422/292 |

Primary Examiner—Robert J. Warden
Assistant Examiner—Krisanne M. Thornton
Attorney, Agent, or Firm—Fay, Sharpe, Beall, Fagan, Minnich & McKee

[57] ABSTRACT

A lid (10) of a countertop decontamination unit (A) is opened to gain access to a tray (12) for receiving items to be sterilized and a well (16) for receiving a two compartment powdered anti-microbial agent carrying cup (C). The cup includes an outer cup portion (50) and an inner cup portion (70) that have peripheral walls (52, 72) affixed together at flanges (54, 74). The outer cup portion (50) is closed at one end by a first detachable base (58). The inner cup portion (70) is closed by a second detachable base (78). The outer and inner cups (50, 70) define a first powdered reagent receiving chamber (56) therebetween. The inner cup defines a second chamber therein. A permeable sheet (100) is affixed to the inner cup portion flange (74) for ventedly sealing both chambers.

18 Claims, 4 Drawing Sheets

TWO COMPARTMENT CUP FOR POWDERED STERILANT REAGENT COMPONENTS

BACKGROUND OF THE INVENTION

The present invention relates to the decontamination art. It finds particular application in conjunction with sterilizing or disinfecting medical instruments and equipment and will be described with particular reference thereto. It will be appreciated, however, that the invention is also applicable to a wide variety of technologies in which at least two components or reagents are kept separate until time of use and then mechanically released.

Decontamination connotes the removal of hazardous or unwanted materials, such as bacteria, mold spores, other pathogenic life forms, radioactive dust, and the like. Disinfection connotes the absence of pathogenic life forms. Sterilization connotes the absence of all life forms, whether pathogenic or not.

Heretofore, medical equipment and instruments have often been sterilized in a steam autoclave. Autoclaves kill life forms with a combination of high temperature and pressure. However, steam autoclaves have several drawbacks. The high temperature pressure vessels tend to be bulky and heavy. The high temperature and pressure tends to curtail the useful life of the endoscopes, rubber and plastic devices, lenses, and portions of devices made of polymeric materials and the like. Moreover, the autoclave sterilizing and cool down cycle is sufficiently long, that multiple sets of the medical instruments are commonly required.

Instruments which cannot withstand the pressure or temperature of the oven autoclave are often sterilized with ethylene oxide gas, particularly in larger medical facilities or hospitals. However, the ethylene oxide sterilization technique also has several drawbacks. First, the ethylene oxide sterilization cycle is even longer than the steam autoclave cycle. Another drawback is that ethylene oxide sterilization is sufficiently sophisticated that trained technicians are commonly required, making it unsuitable for physician and dental offices and for other smaller medical facilities. Yet another drawback is that some medical equipment can not be sterilized with ethylene oxide gas.

Liquid disinfection systems have also been utilized for equipment which could not withstand the high temperatures of steam sterilization. Commonly, a technician mixes a liquid disinfectant composition and manually immerses the items to be decontaminated. The high degree of manual labor introduces numerous uncontrolled and unreported variables into the process. There are quality assurance problems with the weakening of the disinfectant chemicals due to aging on the shelf, technician error in the mixing of sterilants, technician error in the control of the immersion times, technician error between immersion and the rinsing of residue, technician errors in the rinsing of the residue, exposure to the ambient atmosphere after the rinsing step, and the like.

The present invention provides for a new and improved two compartment cup or packaging assembly which is ideal for storing powdered reagents which are retained separately until time of use.

SUMMARY OF THE INVENTION

In accordance with the present invention, a two compartment package is provided. An outer container has a first peripheral wall which has an opening at a first end and at a second end. An inner container has a peripheral wall which has an opening at a first end and a second end. A flange is connected at the first open end of the inner container peripheral wall. The outer and inner containers are configured such that the inner container flange means abuts and is connected adjacent to the outer container's open end. Once the inner cup is inserted and connected to the outer cup, the inner and outer peripheral walls of the inner and outer containers define a first reagent receiving chamber therebetween. The inner container defines a second chamber therein. A closure is connected to the inner container flange. A first detachable base is secured to and closes the second end of the outer container. The first detachable base is detachable in response to a force or pressure applied to it. A second detachable base is secured to and closes the second end of the inner container. The second detachable base is detachable in response to a force or pressure applied to it.

In accordance with another aspect of the present invention, the improvement further comprises a means for maintaining separation between the first and second detachable bases.

In accordance with another aspect of the present invention, the closure is semi-permeable to permit one or both reagents to outgas.

In accordance with yet another aspect of the present invention, the inner container chamber and the outer container chamber are filled with powdered reagents which interact in water to form a strong oxidant and corrosion inhibitors.

In accordance with a more limited aspect of the present invention, one of the outer container chamber and the inner container chamber holds a powdered, water soluble acid precursor and the other holds a powdered borate, other powdered corrosion inhibitors, and a powdered wetting agent.

One advantage of the present invention is that it facilitates materials handling.

Another advantage of the present invention is that it simplifies filling and sealing of two reagents in separate compartments.

Another advantage of the present invention is that it facilitates the handling and shipping of reagents which interact in water to form a strong anti-microbial solution.

Another advantage of the present invention is that it promotes thorough mixing of the reagents and complete dissolving of the reagents.

Other advantages reside in ease of opening, resistance to accidental opening, secure shipping, and the like.

Still further advantages of the present invention will become apparent to those of ordinary skill in the art upon reading and understanding the following detailed description of the preferred embodiment.

BRIEF DESCRIPTION OF THE DRAWINGS

The invention may take form in various components and arrangements of components and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
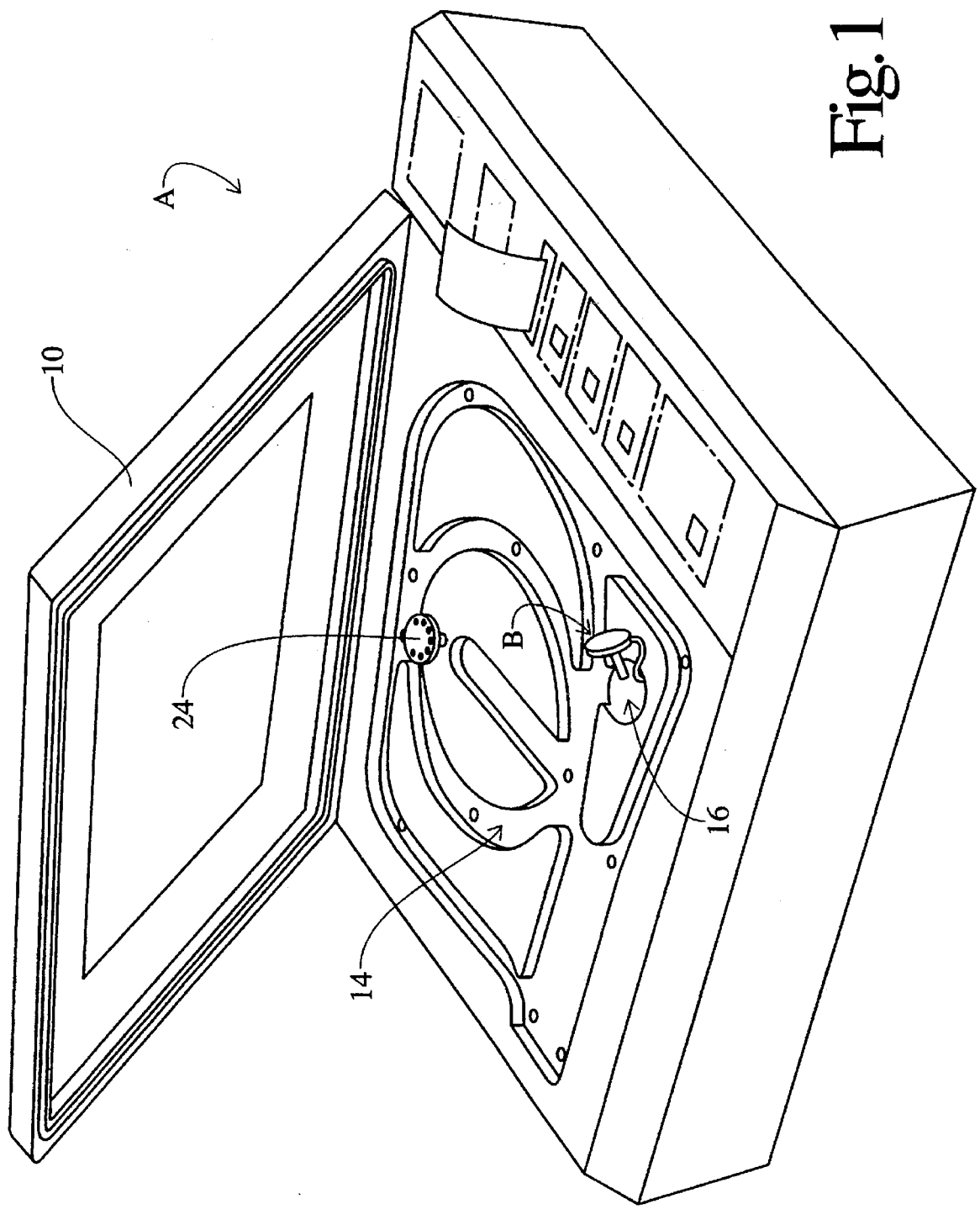
FIG. 1 is an exterior view of a decontamination unit.

With reference to FIG. 1, a microbial decontamination apparatus A is configured to sit on a countertop or other convenient work surface. A door or lid 10 is manually openable to provide access to a tray 12 which defines a receiving region 14 for receiving items to be microbially decontaminated. In the illustrated embodiment, the tray 12 is configured to receive endoscopes or other long, coilable items. Other trays with item receiving regions of different configurations for receiving the items themselves or item holding containers are also contemplated. A well 16 receives a unit dose of reagents for forming a sterilant, disinfectant, or other microbial decontaminating solution.

Figure 2:
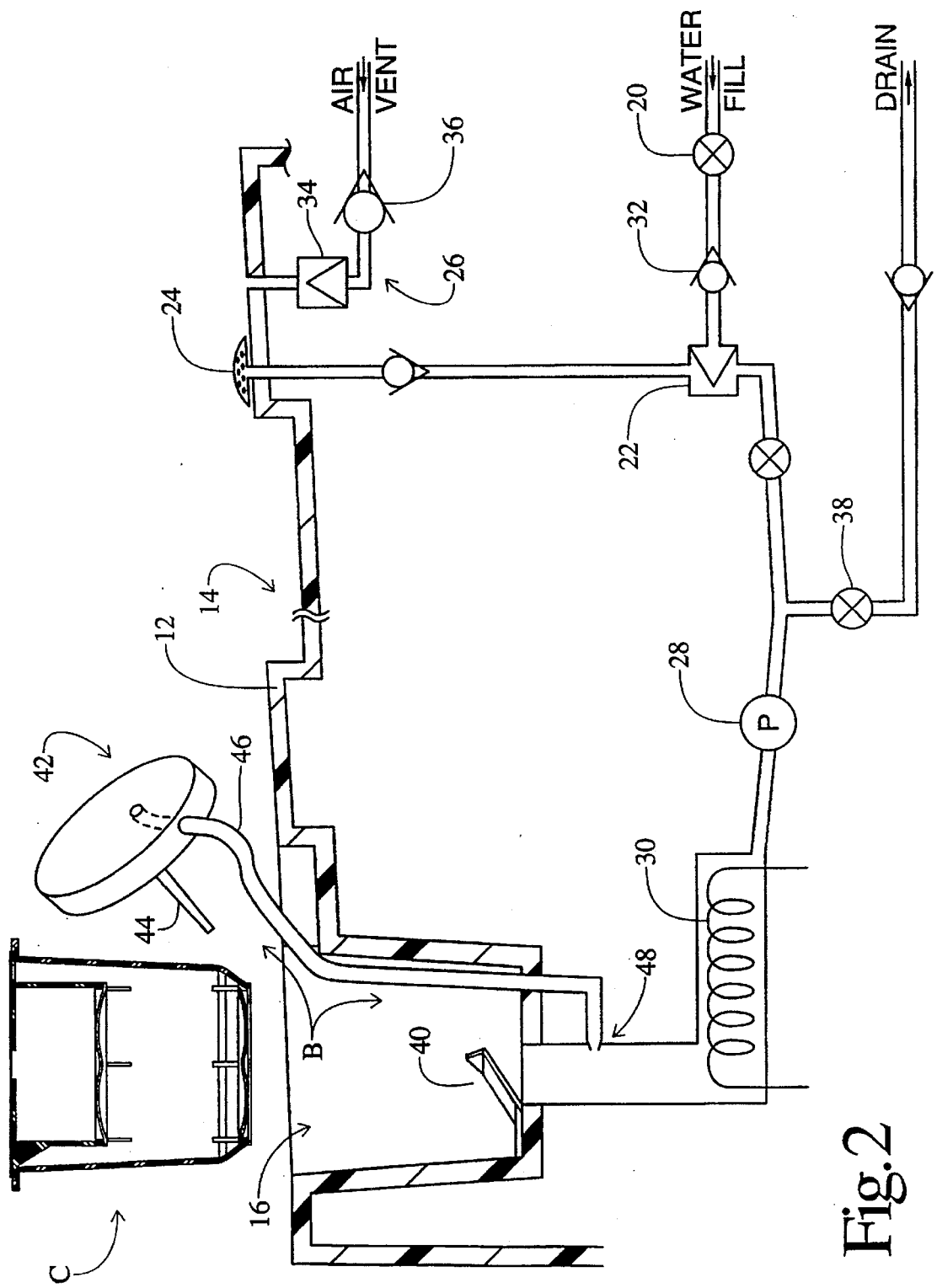
FIG. 2 is a plumbing diagram of the decontamination unit of FIG. 1 including a detailed, cross-sectional view of a reagent cup receiving well, a two-compartment reagent cup, and a cup opening assembly.

With particular reference to FIG. 2, an opener assembly B selectively opens a reagent containing package C as it is inserted into the well 16. Once the items are loaded into the tray and the reagent carrying package C is inserted into the well 16, the lid 10 is closed and latched. A fill valve 20 passes water through a microbe removing filter 22 in flow paths of a fluid circulating system. The microbe removing filter 22 provides a source of sterile water by passing water and blocking the passage of all particles the size of microbes and larger. The incoming water which has been sterilized by the filter 22 passes through a spray or distribution nozzle 24 and fills the item receiving region 14 in the tray 12. As additional water is received, it flows into the well 16 dissolving powdered reagents in the cup C which has been opened forming an anti-microbial solution. Filling is continued until all air is forced through an air system 26 and an entire interior volume is filled with the sterile water. After the fill valve 20 is closed, a pump 28 circulates the fluid through a heater 30, the item receiving region 14 of the tray 12, and the well 16. The pump also forces the anti-microbial solution through the filter 22 to a check valve 32 sterilizing the filter. Further, the pump forces the anti-microbial solution through another microbe filter 34 in the air system 26 to a check valve 36. After the anti-microbial solution has been brought up to temperature and circulated for a selected duration, a drain valve 38 is opened, allowing the solution to drain. Air is drawn through the microbe filter 34 such that sterile air replaces the fluid within the system. Thereafter, the drain valve is closed and the fill valve 20 opened again to fill the system with a sterile rinse fluid. It will be noted, that because the pump 28 circulated the anti-microbial solution over all surfaces of the flow paths including all surfaces leading from the sterile rinse source 22, the rinse cannot bring microbial contaminants into the item receiving region 14.

The opening system B includes a lower opener projection 40 disposed at the bottom of the well for engaging a lower surface of the package C as it is inserted into the well. An upper opener portion 42 has an insertable portion 44 that is connected by flexible tubing 46 with tray 12. After the package C is inserted in the well, the upper opener portion is centered over the package C. The insertable portion 44 is pressed into the center of the package C. The upper opener portion 42 for the connecting tubing 46 has an opening in fluid communication with a venturi 48.

Figure 3:
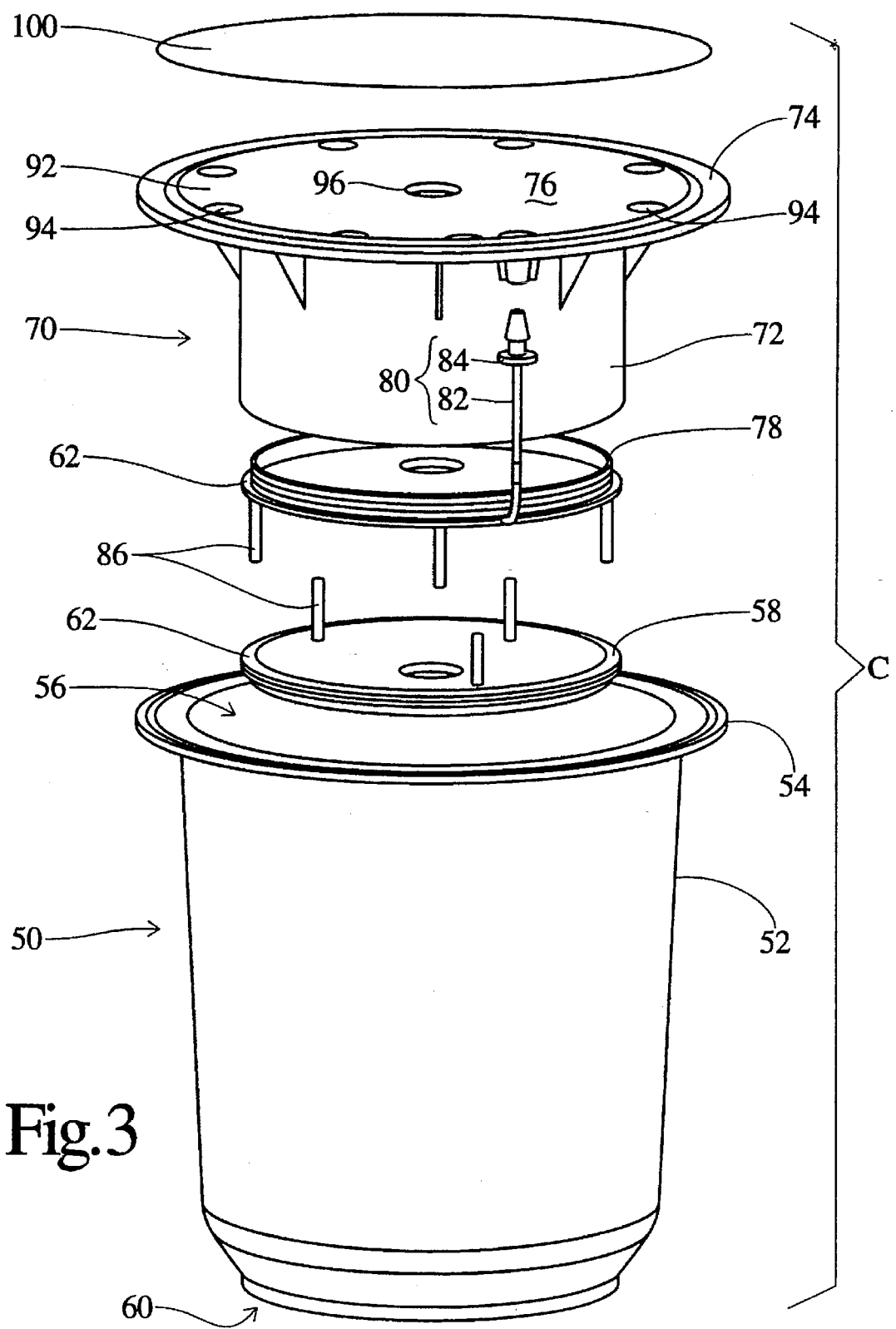
FIG. 3 is an expanded view of a two compartment cup in accordance with the present invention; and, FIG. 4 is a side sectional view of the two compartment cup.
Figure 4:
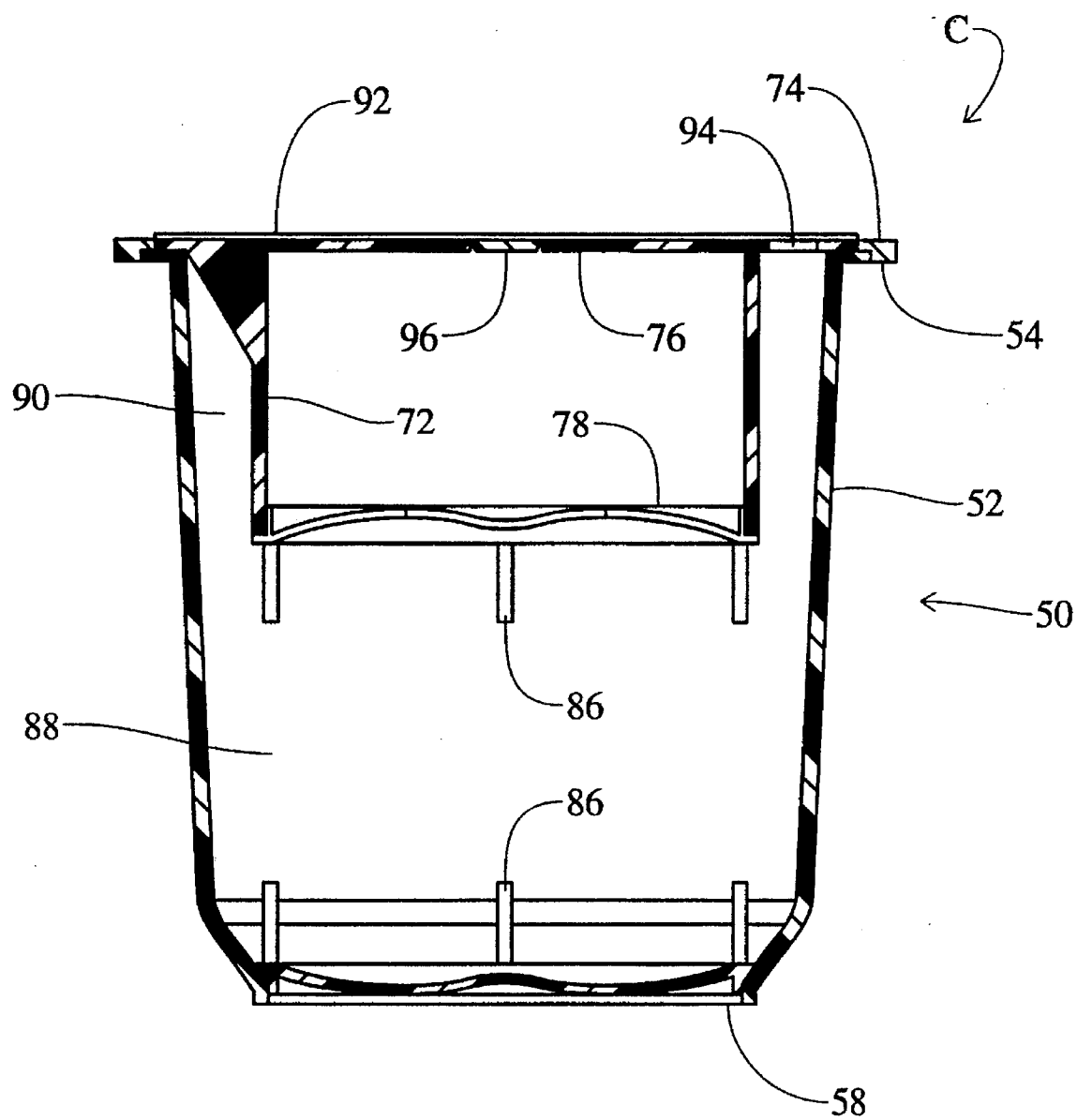

With reference to FIGS. 3 and 4, the sterilant cup or package C includes a first or outer cup 50. The outer cup is constructed of a light weight, rigid polymeric material. The outer cup 50 includes a cylindrical peripheral wall 52 that has a flange 54 at a first, open end 56 thereof. A first detachable base wall 58 closes a second, opposite end 60 of the peripheral wall 52. The first detachable base wall 58 is secured to the second end by being snapped in and held by a lip and groove, friction engagement, a breakable seal, or the like. When force or pressure is applied to the first detachable base wall from beneath the outer cup 50 by the lower opener member 40, the first detachable base wall 58 detaches. An enlarged flange 62 or the like retains the base wall in the interior of the outer cup by making the diameter of the base wall larger than the opening at the second end. The detached base wall 58 opens the second end of the outer cup allowing fluids such as a dilutant to enter and mix with the contents of the outer cup 50.

A second or inner cup portion 70 is received in the first cup portion 50. The second cup portion has a generally cylindrical peripheral wall 72 that has an integrally molded flange 74. The second cup portion is sealed at a first or top end by a second chamber top wall 76. A second detachable base wall 78 closes a second end of the peripheral wall 72. The second detachable base wall is secured to the second end of the inner cup 70 by being snapped in and held by a lip and groove, friction fit, a breakable seal, or the like. When a force or pressure is applied by an insertable member 42 extending through the first end of the inner cup 78 and onto the second detachable base wall 78, the second detachable base wall 78 detaches from the peripheral wall 72. The detached base wall 78 opens the inner cup second end allowing the contents of the inner cup 70 to mix with the contents of the outer cup 50.

The first detachable base wall 58 and the second detachable base wall 78 each have a domed central region. The domed central region is surrounded by a vertical wall that frictionally engages the peripheral wall of the cup. As force is applied to the domed central region, it flexes. The flexing urges the attached vertical wall away from the peripheral wall of the cup producing the frictional engagement and facilitating its release.

In the preferred embodiment, a retaining means 80 is connected to the second base wall to retain it in the first cup and prevent it from blocking the open end. The retaining means includes an elongated retainer or strap 82 attached to the second cup by a collar 84 and an enlargement at one end and attached at the other end to the second base wall 78.

A plurality of legs 86 or other spaced projections are provided on the first and second base walls. The legs hold the base walls in a spaced relationship to prevent powdered reagents or a slurry of partially dissolved reagents from becoming trapped between the base walls.

With continuing reference to FIGS. 3 and 4, the first and second cup portions are configured such that the flanges 54, 74 abut and are sealed together. Appropriate sealing means for the flanges include adhesive bonding, solvent welding, ultrasonic welding, or the like.

Preferably, the inner cup peripheral wall 72 is about half the height of the outer cup peripheral wall 52 such that a first reagent chamber 88 is defined therebetween. More specifically to the illustrated embodiment, the chamber 88 has a predetermined volume ratio relative to a volume of the inner cup 70. Although various second cup peripheral wall designs may be utilized to achieve the selected relative volume ratio between the chamber 88 and the second cup volume, a circular wall surface is preferred.

The second chamber within the inner cup 70 is smaller in diameter than the first chamber 88 such that an annular passage 90 is defined therebetween. The second chamber top wall 76 has a peripheral overhang 92 extending outward beyond the upper cup. Vent apertures 94 are defined in the overhang 92 in communication with the annular passage 90. The vent apertures 94 enables the reagents stored in the lower cup portion to outgas. The top wall second chamber 76 also has a central plug 96 which snaps open under pressure from the insertable member 44 to form an aperture in communication with the interior of the second cup. The central aperture 96 also provides a guide for the upper opener portion 44. Optionally, the plug 96 may be porous if the reagents in the second cup outgas.

A porous closure 100, such as TYVEC™ material, is adhered to the second chamber top wall 76 to seal the two chambers against powder loss. In the preferred embodiment in which one of the powders liberates gas during storage, the closure 100 is a flexible layer of a permeable material. In other applications, the closure 100 may be a flexible sheet of impermeable foil, plastic, or the like. As yet another alternative, the closure 100 may be impermeable except for a small aperture or pin prick, a section of permeable material, or the like. This permits one of the chambers to be outgassed while retaining the other hermetically sealed from ambient humidity. Optionally, the closure may include a pull tab to facilitate pealing off the closure for manual emptying of the contents.

In the preferred embodiment, the inner and outer cups each contain one of an acid precursor and a persalt. More specifically to the preferred embodiment, the acid precursor is acetylsalicylic acid and the persalt is sodium or other perborates. When the first and second detachable bases 58 and 78 are detached, the two compounds come into contact and react in the presence of water to form sodium metaborate, peracetic acid, and salicylic acid. With the detachable bases, the compounds are completely released from their respective chamber with no trappings remaining.

The volume of powdered ingredients is selected relative to the volume of water such that a 0.2% W/V concentration of peracetic acid is achieved in the resultant decontamination solution. The sodium metaborate solution functions as an inorganic corrosion inhibitor and the salicylic acid is an organic corrosion inhibitor. Preferably, additional corrosion inhibitors, buffers, and a wetting agent are added to these powders. Preferred copper and brass corrosion inhibitors include azoles, benzoates, other five-membered ring compounds, benzotriazoles, tolytriazoles, mercaptobenzathiazole, and the like. Other anti-corrosive buffering compounds include phosphates, molybdates, chromates, dichromates, tungstates, vanidates, other borates, and combinations thereof. These compounds are effective for inhibiting steel and aluminum corrosion. For hard water in which calcium and magnesium salts may tend to precipitate, a sequestering agent such as sodium hexametaphosphate is also included. Other dry formulations can be utilized to generate chloride gas, hydrogen peroxide, hypochlorous acid, and other strong oxidants which have a biocidal effect.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. In a two compartment package for holding powdered reagents which interact in water to form an anti-microbial solution, the package including (i) an outer first cup portion having a first peripheral wall which has an opening at a first end and at a second end, (ii) an inner, second cup portion having a second peripheral wall, an overhanging flange connected at a first end of the second peripheral wall, a closure covering the first end of the second peripheral wall, and having a second end of the second peripheral wall, the first and second cup portions being configured such that the second cup portion flange abuts and is connected to the first end of the outer first cup portion, the first and second peripheral walls being configured such that a first powdered reagent receiving chamber is defined in the first cup portion and a second chamber is defined in the second cup portion, the improvement comprising:

a first detachable base portion secured to and closing the second end of the outer first cup portion, the first detachable base portion being detachable by applying a force to the first detachable base portion; and, a second detachable base portion secured to and closing the second end of the inner, second cup portion, the second detachable base portion being detachable by applying a force to the second detachable base portion.

2. In a two compartment package for holding powdered reagents which interact in water to form an anti-microbial solution, the package including (i) an outer first cup portion having a first peripheral wall which has a first opening at a first end and a second opening at a second end, (ii) an inner, second cup portion having a second peripheral wall, an overhanging flange and a cover connected at a first end of the second peripheral wall and having a second end of the second peripheral wall, the first and second cup portions being configured such that the second cup portion flange abuts and is connected to the first cup portion first end, the first and second peripheral walls being configured such that a first powdered reagent receiving chamber is defined in the first cup portion and a second chamber is defined in the second cup portion, the improvement comprising:

a first means for mechanically engaging and closing the second end of the outer first cup portion, the first means releasing the mechanical engagement under application of an axial force to detach the first means from the outer first cup portion;

a second means for mechanically engaging and closing the second end of the inner, second cup portion, the second means releasing the mechanical engagement under an axial force to detach the second means from the inner second cup portion; and, a means for retaining the first and second means in a spaced relationship after the second means is detached from the second cup portion.

3. In the package as set forth in claim 1, the improvement further comprising:

a plurality of projections on at least one of the first and second base portions which hold the base portions in at least a partially spaced relationship.

4. In the package as set forth in claim 1, the improvement further comprising:

a means for retaining the second detachable base portion within a predetermined distance from the second end of the second peripheral wall after the second detachable base portion is detached from the second cup.

5. A two compartment package for holding reagents, the package including (i) an outer first cup portion having a first peripheral wall which defines a first opening at a first end and a second opening at a second end, (ii) an inner, second cup portion having a second peripheral wall, an overhanging flange connected at a first end of the second peripheral wall and having a second end of the second peripheral wall, the first and second cup portions being configured such that the second cup portion flange abuts and is connected to the first cup portion first end, the first and second peripheral walls being configured such that a first reagent receiving chamber is defined in the first cup portion and a second chamber is defined in the second cup portion, the package further comprising:

a first detachable base portion secured to and closing the second end of the outer first cup portion, the first detachable base portion being released by an applied force and having a flange on an inner side thereof which flange is larger than the second opening at the second end of the first cup portion such that the first base portion is trapped in the first chamber after the first base portion is detached from the first cup portion; and a second detachable base portion secured to and closing the second end of the inner second cud portion, the second detachable base portion being released by an applied force to the second detachable base portion.

6. A two compartment package for holding reagents, the package comprising:

an outer first cup portion having a first peripheral wall which has a first opening defined at a first end and a second opening defined at a second end;

a first detachable base portion secured to and closing the second opening of the outer first cup portion, the first detachable base portion being detachable by an applied force;

an inner second cup portion having a second peripheral wall, an overhanging flange connected at a first end of the second peripheral wall and an opening defined at a second end of the second peripheral wall, the first and second cup portions being configured such that the second cup portion flange abuts and is connected to the first cup portion first end, the first and second peripheral walls being configured such that a first reagent receiving chamber is defined in the first cup portion and a second chamber is defined in the second cup portion;

a second detachable base portion secured to and closing the opening defined at the second end of the inner second cup portion, the second detachable base portion being detachable by an applied force to the second detachable base portion, at least one of the first and second cup portion base portions having a domed central portion surrounded by a circumferential wall that engages the second end of the peripheral wall, such that flexing of the dome reduces engagement force between the second end of the peripheral wall to facilitate removal of the base portion.

7. A two compartment package for holding reagents, the package including (i) an outer first cup portion having a first peripheral wall which has a first opening at a first end and a second opening at a second end, (ii) an inner second cup portion having a second peripheral wall, an overhanging flange and a top wall connected at a first end of the second peripheral wall and having an opening at a second end of the second peripheral wall, the first and second cup portions being configured such that the second cup portion flange abuts and is connected to the first cup portion first end, the first and second peripheral walls being configured such that a first reagent receiving chamber is defined in the first cup portion and a second chamber is defined in the second cup portion, the package further comprising:

a first detachable base portion secured to and closing the second opening at the second end of the outer first cup portion;

a second detachable base portion secured to and closing the opening at the second end of the inner, second cup portion; and, the first and second cup portions defining an annular gap therebetween and the top wall of the second cup portion defining a vent aperture in communication with the annular gap.

8. In the package as set forth in claim 7, the improvement further comprising:

a porous filter material covering the vent aperture.

9. A two compartment package for holding powdered reagents which interact in water to form an anti-microbial solution, the package comprising:

an outer first cup portion having a first peripheral wall which has a first opening at a first end and a second opening at a second end;

a first detachable base portion secured to and closing the second opening at the second end of the outer first cup portion, the first detachable base portion being releasable by applying a force to the first detachable base portion;

an inner, second cup portion having a second peripheral wall, an overhanging flange connected at a first end of the second peripheral wall and having an opening at a second end of the second peripheral wall, the first and second cup portions being configured such that a first powdered reagent receiving chamber is defined in the first cup portion and a second chamber is defined in the second cup portion, one of the chambers holding an acid precursor and the other chamber holding a persalt;

a second detachable base portion secured to and closing the second opening at the second end of the inner second cup portion, the second detachable base portion being releasable by applying a force to the second detachable base portion.

10. In the package as set forth in claim 9, wherein the acid precursor includes acetylsalicylic acid and the persalt includes sodium perborate.

11. In the package as set forth in claim 1, the improvement further comprising:

the closure including a thin sheet of permeable material.

12. In the package as set forth in claim 11, the improvement further comprising:

the first and second cup portions being constructed of plastic material.

13. A method comprising:

providing a first cup having a first cup peripheral wall which has an opening at a first end and is closed by a first detachable base wall at a second end;

inserting a second cup into the first cup, the second cup including: a second cup peripheral wall, a flange connected at a first end of the second cup peripheral wall, and a second detachable base wall integrally connected to a second end of the second cup peripheral wall, the first and second cups being configured such that when the second cup is inserted into the first cup, the second cup flange abuts the first cup open end, the first and second cup peripheral walls defining a first powdered reagent receiving chamber therebetween and the second cup defining a second chamber therein;

connecting the second cup flange to the first cup first end;

metering a preselected volume of a first powdered reagent into the first chamber;

metering a preselected volume of a second powdered reagent into the second chamber;

sealing a closure to the second cup flange surrounding the second cup such that the first and second chambers are sealed concurrently.

14. The method as set forth in claim 13 further including:

transporting the sealed cups and the contained powdered reagents to a site at which decontamination is to be performed;

applying a force to both the first and second detachable base walls to detach the base walls from the first and second cups, respectively;

mixing the first and second powdered reagents with water to form a decontamination solution; and, immersing items to be decontaminated in the decontamination solution.

15. The method as set forth in claim 14 wherein the powdered reagents in one of the first chamber and the second chamber include an acid precursor and the powdered reagents in the other include a persalt.

16. The method as set forth in claim 15 wherein the acid precursor includes acetylsalicylic acid and the persalt includes sodium perborate.

17. A decontamination system comprising:

a powdered reagent cup receiving well;

a first fluid flow path defined between a water receiving inlet and the reagent cup receiving well to bring water from the inlet to the well to mix with powdered reagents and form a decontaminant solution;

a second fluid flow path being defined for the decontaminant solution from the reagent cup receiving well to a decontamination region for receiving items to be decontaminated;

a third fluid flow path being defined from the decontamination region to a drain outlet for selectively draining spent decontamination solution and water;

a fluid circulator for selectively circulating fluid through the first, second, and third fluid flow paths and among the inlet, the decontamination region, and the reagent cup receiving well;

a two-chamber powdered decontamination reagent holding cup for insertion into the well, the cup including:

(i) an outer first cup portion having a first peripheral wall which has an opening at a first end and being closed by a first openable base wall at a second end, (ii) an inner, second cup portion having a second peripheral wall, a flange connected at a first end of the second peripheral wall and being closed by a second openable wall at a second end of the second peripheral wall, the first and second cup portions being configured such that the second cup portion flange abuts and is connected to the first cup portion open end, the first and second peripheral walls being configured such that a first powdered reagent receiving chamber is defined in the first cup portion and a second chamber is defined in the second cup portion, and (iii) a closure which closes the second cup portion flange;

a lower opener projection disposed adjacent and extending into the cup receiving well for engaging and releasing the first base wall; and, an upper opener projection disposed adjacent the cup receiving well for manual movement through the closure to engage and release the second base wall.

18. A method for decontamination comprising:

transporting a reagent package which include an outer first cup portion having a first peripheral wall which has a first opening at a first end and a second opening at a second end, a first detachable base portion secured to and closing the second opening at the second end of the outer first cup portion, an inner second cup portion having a second peripheral wall, an overhanging flange connected at a first end of the second peripheral wall and having an opening at a second end of the second peripheral wall, the first and second cup portions being configured such that a first chamber holding a first reagent is defined in the first cup portion and a second chamber holding a second reagent is defined in the second cup portion, a second detachable base portion secured to and closing the second opening at the second end of the inner second cup portion to a site at which decontamination is to be performed;

applying a detaching force to both the first and second detachable base walls to detach the base walls from the first and second cups, respectively;

mixing the first and second reagents with water to form a decontamination solution; and, immersing items to be decontaminated in the decontamination solution.

* * * * *